Figure 1:
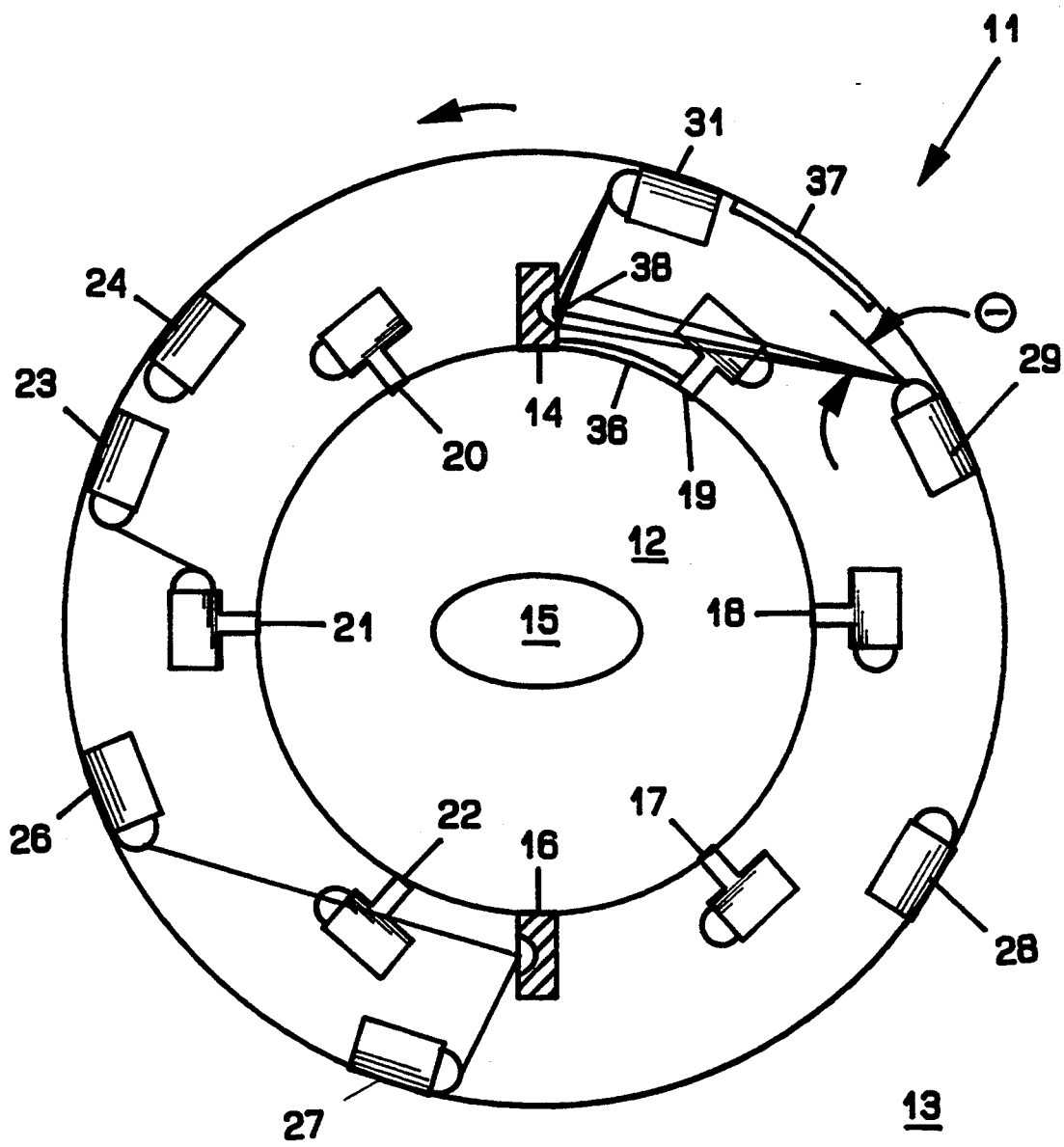

United States Patent [19]

Kedmi et al.

[11] Patent Number: 5,354,993
[45] Date of Patent: Oct. 11, 1994

[54] OPTICAL COMMUNICATION LINK FOR MEDICAL IMAGING GANTRY HAVING CONTINUOUS LINE OF SIGHT COMMUNICATIONS BETWEEN TRANSMITTERS AND RECEIVERS

[75] Inventors: Shmuel Kedmi; Joseph Bodenheimer, both of Jerusalem; Yoav Kanfi, Herzelia, all of Israel

[73] Assignee: Elscint Ltd., Haifa, Ireland

[21] Appl. No.: 894,574

[22] Filed: Jun. 5, 1992

[30] Foreign Application Priority Data

Jun. 9, 1991 [IL] Israel .......................... 098421

[51] Int. Cl.⁵ .................................. G02B 27/00
[52] U.S. Cl. .................................. 250/551; 378/19
[58] Field of Search .................... 250/551; 378/15, 19, 378/4, 196

[56] References Cited

U.S. PATENT DOCUMENTS 4,259,584  3/1981  Krumme .
4,796,183  1/1989  Ermert et al. .
4,912,735  3/1990  Beer .
5,134,639  7/1992  Vekstein et al. .................... 378/19

Primary Examiner—David C. Nelms
Assistant Examiner—Que T. Le
Attorney, Agent, or Firm—Sandler Greenblum & Bernstein

[57] ABSTRACT

A system that enables the communication of data and control signals between the rotor and the stator of a gantry using light transmitters and light receivers. The transmitters are attached to the gantry is such a manner that the light beams are transmitted in a direction that traverses the radial direction of the rotor of the gantry and also traverses a line parallel to the axis of rotation of the rotor. Further, the light beam from the transmitter to the receiver is shaped to minimize the dynamic range of the light flux variation. The light beams from transmitter to receiver are substantially direct line of sight beams and are not reflected through any light channels or carried in any optical transmitting means such as fibre glass.

19 Claims, 3 Drawing Sheets

OPTICAL COMMUNICATION LINK FOR MEDICAL IMAGING GANTRY HAVING CONTINUOUS LINE OF SIGHT COMMUNICATIONS BETWEEN TRANSMITTERS AND RECEIVERS

FIELD OF THE INVENTION

The present invention relates to optical communication systems and more particularly to such systems applicable to computerized tomographic (CT) scanners. Examples of such scanners are X-ray CT scanners and single photon emission CT (SPECT) scanners, both used in medical imaging. The optical communication systems of the present invention efficiently and reliably transfer data and/or control signals between a stationary member and a rotatable member in the CT scanners.

BACKGROUND OF THE INVENTION

Most scanners used in X-ray or in nuclear medicine computerized tomography have a radiation detector mounted on a rotor which rotates about a patient to acquire data. The data is employed in reconstructing a tomographic or planar image of a desired section of the patient.

In X-ray computerized tomography the scanners in present use are designed to operate as either rotate-rotate ("third generation") scanners or "rotate-only" ("fourth generation") scanners. In both cases a gantry including the rotor and stator are provided with a central axial aperture concentric with the axis of rotation of the rotor. The aperture is designed to conveniently receive a normal person in a prone position.

Data from the detector when mounted on the rotor must be transferred to processing equipment that remains stationary. In addition, operating power and control signals have to be supplied to the rotor to control the operation of an X-ray tube, among other things.

In SPECT scanners the gamma ray camera head or detector is mounted on a rotatable portion of a stationary ring to enable the gamma camera head to circle the patient. Thus, data is acquired from many different rotational angles about the patient thereby enabling reconstruction of a tomographic image. Here again, control signals and operating power are required for operation of the camera head and data from the camera head must be transferred from the rotary ring to the computer of the gamma camera system which remains stationary.

Conventionally, the required power and data including control signals are transmitted to and from the rotatable member both in the X-ray scanner and the nuclear medicine scanners via flexible high-voltage cables for the power and shielded cables for the control signals and the data. Cable uptakes or spooling systems have been provided which enable at least one complete rotation of the rotatable member to occur.

More recently, new designs have been used for transferring both data and power to and from the rotatable member. See, for example, U.S. Pat. No. 4,912,735, entitled "Power Apparatus Particularly for CT Scanners", which issued on Mar. 27, 1990, and which is assigned to the Assignee of this invention. That Patent describes unique inductive power transfer methods which enable discarding flexible cables and the spooling systems for the transmission of power in X-ray computerized tomography.

However, until the invention of the copending U.S. application Ser. No. 785,056 filed Oct. 30, 1991 data and control signal communications between the rotating and stationary parts of the system for acquiring SPECT images always used flexible cables and/or cable pulley systems attached to the rotatable portion of the scanning apparatus. The system of the aforementioned Patent Application taught the possibility of SPECT scanners to rotate more than once about the patient.

Data and control signal communication apparatus coupling rotating and stationary portions of gantries, particularly for X-ray CT scanners, are found for example in U.S. Pat. No. 4,796,183 which covers a system that transmits data between a rotor and a stator utilizing a wave guide attached to the rotor.

Another pertinent data and control signal inter-communication system is described in U.S. Pat. No. 4,259,584. There data generated by the detector of a CT scanner is transmitted to stationary processing equipment using a ring of light conducting material bent around the center of rotation of the rotatable member to form a ring. A light source emits light signals that correspond to the data signals. The emitted light signals are transmitted on to the ring of light conducting material. The ring conducts the light signals over its circumference to a coupling location at which a light receiver is located on the stationary part of the scanner.

A light utilizing system for communicating data and control signals between a stator and a rotor is the system disclosed in U.S. Pat. No. 5,134,639 issued Jul. 28, 1992 and which is assigned to the Assignee of this Application. That Application utilizes a hollow tube having a reflective inner surface for transmitting data and control signals on modulated light beams between a rotating member and a stationary member of a computerized tomographic system.

In summary, the pertinent prior art on data and control signal communications between rotor and stator using light as the communicating media shows two different modes for the transmission of data and/or control signals. In one mode light conducting material curved around the center of rotation is used (U.S. Pat. No. 4,259,584). The other mode is that of U.S. Pat. No. 5,134,639 which teaches the use of hollow tubes with reflective inner surfaces with the light being projected axially.

Thus, the prior art transmits control and data signals to and from the rotating part of the gantry in a manner enabling continuously rotating the gantry over many revolutions without having to reverse and return to the zero degree point after each revolution as was required when cables were used for coupling the rotary part of the gantry to the stationary part of the gantry. However, the prior art used for transmitting signals to and from the rotary part of the gantry either features limiting solid light transmitting material, or delicately machined hollow tubes.

The problem of providing optical communication links between the rotor and stator of medical imagine gantries imposes severe restraints. For example, there is a space constraint which limits the transmission medium to a circular ring shaped cavity. The rotor and the stator transmitters and receivers must move within this cavity each describing a circle of rotation without obstructing each other while maintaining continuous communication between stator and rotor. At the same time there should be no cross-talk between transmitter and receivers of the same unit; i.e., stator or rotor.

Since the use of the transmitted data is critical, there is a requirement of extremely low bit error rate; i.e., BER $10^{-12}$. This makes it preferable that the light flux from transmitter to receiver be optimized. Optimization in this context means not only maximum signal-to-noise ratio at the detector, but especially minimization of the dynamic range of the light flux variation.

BRIEF DESCRIPTION OF THE INVENTION

Accordingly, it is an object of the present invention to provide for communicating data and control signals between the rotary part and the stationary part of a gantry used in medical imaging systems in a simple, effective and inexpensive manner taking into consideration the above described restraints.

A feature of the invention enables the transmission of both control signals from the stationary part of the gantry to the rotary part of the gantry and data and/or control signals from the rotary part of the gantry to the stationary part of the gantry using direct line of sight communications between light transmitter means and light receiver means. The light receiver means and the light transmitter means in a preferred embodiment are mounted both on the stator and on the rotor of the gantry in a manner to enable two-way communications between the stator and the rotor even when the rotor is stationary.

In accordance with a broad aspect of the present invention, an optical communication link ("OCL") coupling the rotating part to the stationary part of the gantry is provided. The gantry is used, for example, for obtaining tomographic images in medical diagnostic imaging systems. The communication link includes communicating means for transmitting data and control signals between the stationary and the rotary parts of the gantry, said communicating link comprising:

- means for converting electrical signals to light signals,
- transmitter means for transmitting said light signals,
- receiving means for receiving said transmitted light signals,
- the transmitter means and the receiving means being mounted on the rotor and the stator so that there is direct line of sight linkage between the transmitter means and the receiving means,
- means for converting the light signals received by said receiving means to electrical signals, and
- means for using said electrical signals for such things as data processing to provide images or for control purposes.

A feature of the present invention comprises:

- means for using a transmitter mounted on a rotor to transmit light waves to a receiver mounted on a stator when the rotor transmitter and the stator receiver are in line of sight with each other, and
- means for assuring that there is always at least one rotor transmitter in the line of sight with at least one stator receiver as the rotor rotates or even when the rotor is stationary.

A feature of the invention includes the means for causing the transmitters to continuously transmit even when there is no data. The continuous transmission maintains synchronization and alerts against any problems.

Another feature of the invention comprises utilizing a plurality of stator transmitters to enable continuous flow of control data from said stator to said receiver.

According to yet another feature of the present invention, the light transmitter means includes a light emitting diode (LED) and the light detecting or receiving means includes a photosensitive diode.

According to still another feature of the invention, the stator receivers and stator transmitters can be positioned so that a plurality of channels of communications between said rotor and said receiver are established.

According to yet another feature of this invention, the beam from the transmitter to the receiver is shaped to aid in optimizing the flux transfer from the transmitter to the receiver so as to maximize signal-to-noise ratio while minimizing the dynamic range of the light flux variation.

Another feature of the invention deflects the angle of the transmitter axis from the circumferential loci of rotation to improve light flux transfer.

Still another feature of the present invention is the use of reflective material on the stator and/or rotor to optimize flux transfer in the above mentioned sense.

Yet another feature of the present invention is the use of a plurality of receivers with the transmitter to increase the capacity of information transferable with a given number of transmitters.

Still another feature of the invention is the utilization of rotor to stator transmission in a direction opposite to the direction of transmission of stator to rotor information.

Figure 2:
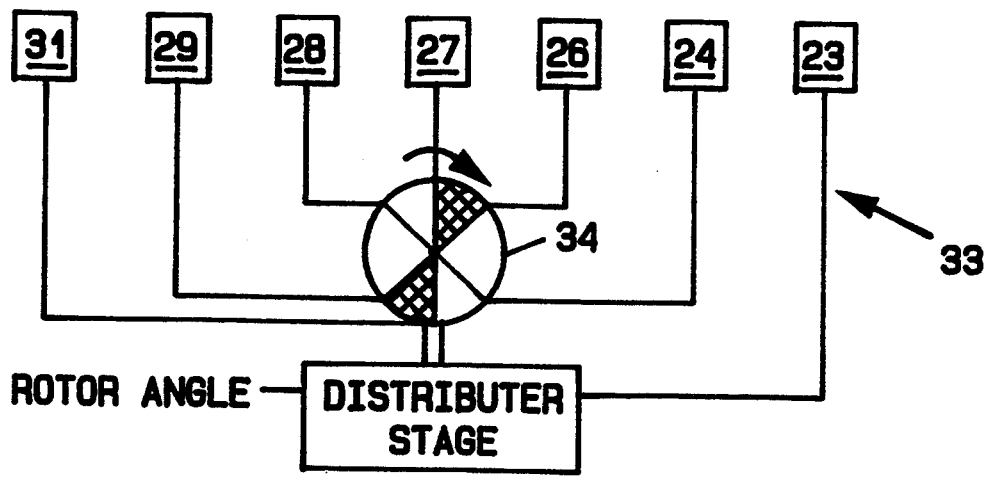
Figure 3:
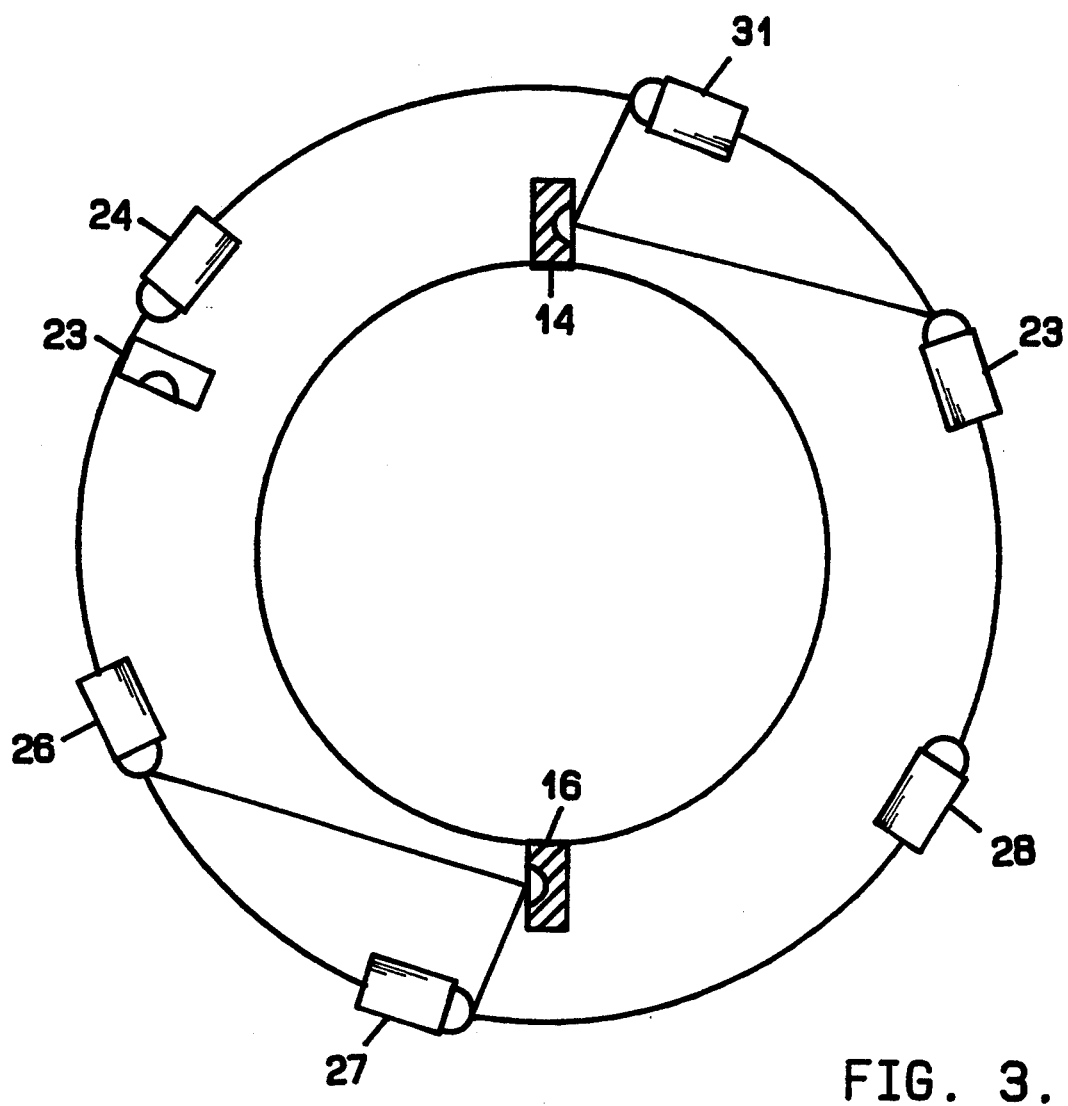
Figure 4A:
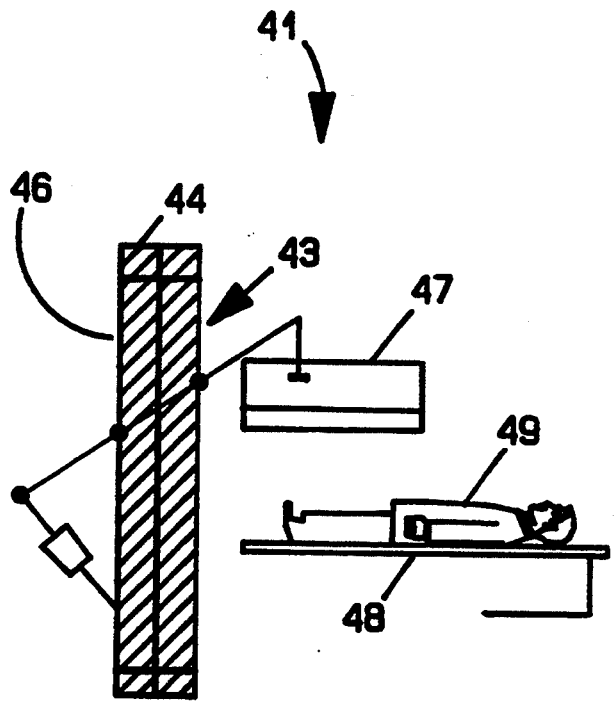
Figure 4B:
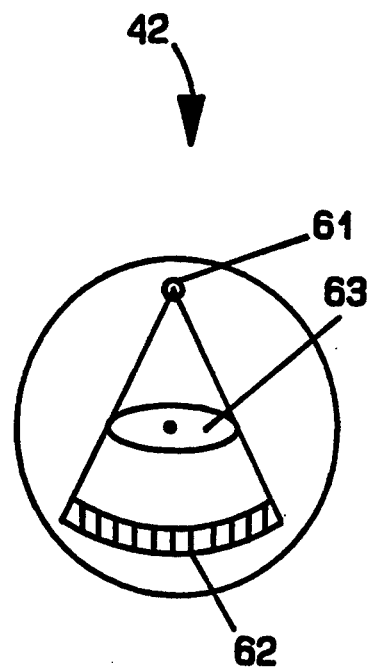
Figure 4C:
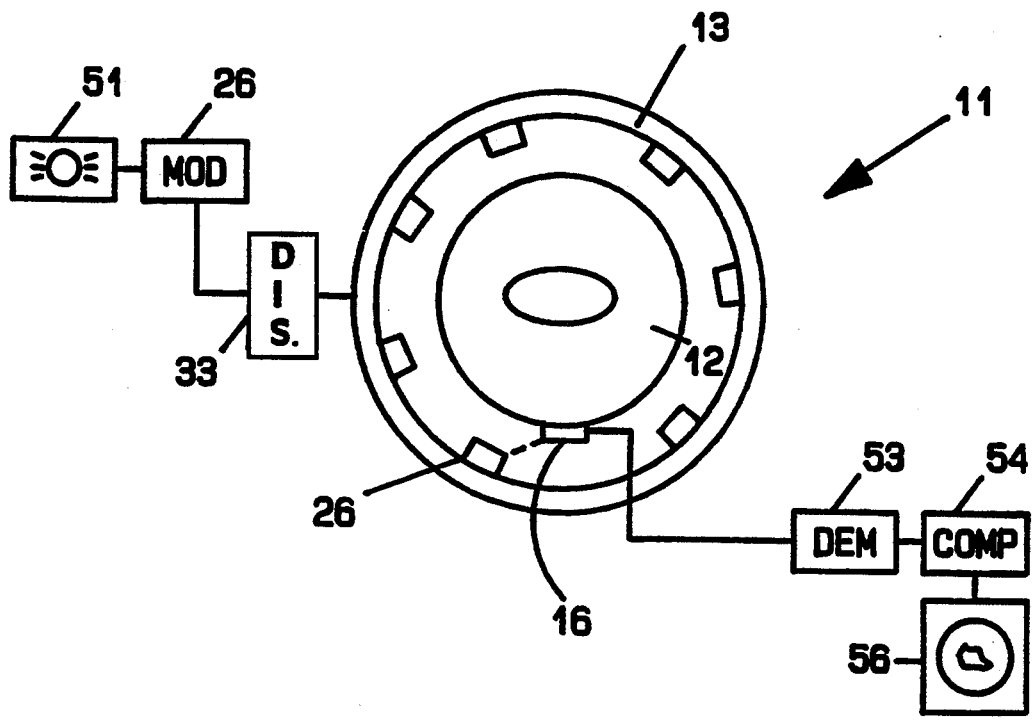

The above features and other features and objects of the present invention will be best understood when considered in the light of the following description made in conjunction with the accompanying drawings; wherein:

FIG. 1 shows a preferred optical communication link ("OCL") system configuration, FIG. 2 shows a distributor used in the system configuration of FIG. 1, FIG. 3 shows a basic arrangement of rotor to stator communications using the OCL system of FIG. 1, and FIG. 4A schematically shows the use of the system for nuclear medicine computerized tomography;

FIG. 4B schematically shows the use of the system for X-ray computerized tomography; and FIG. 4C schematically shows the use of the system for nuclear medicine computerized tomography.

GENERAL DESCRIPTION

The stator rotor arrangement 11 of FIG. 1 includes a stator 12 central to the rotor 13. In computerized tomographic systems, the stator has a hollow section or aperture 15 wherein a patient can be inserted so that data can be acquired from the patient. The stator 12 is shown as having a plurality of receivers mounted thereto. More particularly, there are two receivers shown at 14 and 16 mounted 180° apart. The number of channels for data is determined by the number of receivers. Thus, where one channel is sufficient only one stator receiver is required.

A plurality of stator transmitters are shown mounted on the stator. More particularly, stator transmitters 17, 18, 19, 20, 21 and 22 are shown mounted with 60° separating each of the transmitters. These transmitters communicate with the same rotor receiver 23. The stator transmitters and rotor receivers are all in the same axial plane.

In a different axial plane are shown six rotor transmitters 24, 26, 27, 28, 29 and 31 in the same axial plane as these rotor transmitters, a pair of stator receivers 14, 16 are shown. The rotor transmitters are shown spaced apart from each other by 60°. The number of transmitters and thus spacing between the transmitters necessary for continuous line of sight communications between the transmitters and the receivers are determined by the radial spacing between the stator and the rotor and the angle of the transmitted light beam relative to the loci of the centerline of the rotor transmitter as the rotor rotates relative to the stator.

It should be understood that the showing of the transmitters and receivers on the stator and rotor are by way of example only both the numbers and the spacings can be changed within the scope of the present invention.

As the rotor rotates around the stator, a distributor 33, as shown in FIG. 2, causes different rotor transmitters to transmit the data acquired by the rotating detector to the stator where the data is used. In the particular example described herein, the data is operated on and processed to form an image. A mechanical distributor is shown wherein the cross hatched sections of the distributor rotor rotating in the clockwise direction transmits data to the transmitters. The transmitted data is received by the stator receivers 14 and 16. Thus, as shown in FIG. 1 as the rotor rotates in a counter-clockwise direction, for example, the transmitter 27 will be transmitting along the line of sight between the transmitter 27 and the stator receiver 16 until the rotor transmitter 27 passes the line of sight position for transmitting data to the receiver 16. Shortly before that time, the next rotor transmitter in the succession of rotor transmitters; i.e., rotor transmitter 26 starts to transmit its data to the stator receiver 16.

Thus, in a preferred embodiment there are a few degrees of overlap between the transmissions of rotor transmitter 27 and rotor transmitter 26. The overlap assures that the there is continuous transmission of data between the rotor and the stator. Subsequently, the rotor transmitter 24 will be in a position for line of sight communications with receiver 16 as rotor 13 rotates around the stator 12. Then the rotor transmitter 24 will start transmitting data to the data receiver 16.

It should be understood that while rotation of the rotor of the CT gantry in a counter-clockwise direction is described, such direction is specified only by way of example. The rotational direction could also be clockwise with transmitters and receivers rotated 180° within the scope of the present invention.

A feature of the invention has the rotor transmitters facing in a counter-clockwise direction towards stator receivers facing in a clockwise direction. The transmitters are facing in an opposite direction to the direction faced by the rotor transmitter (i.e.; clockwise). Similarly, the rotor receivers face the counter-clockwise direction. This means for assuring that the rotor-to-stator information is transmitted in an opposite circular direction to the stator-to-rotor information eliminates cross talk.

The starting and stopping of the operation of transmitters is controlled by distribution means such as the distributor 33 shown in FIG. 2. As the gantry rotor rotates the distributor including the rotating data transmitting arrangement 34 causes different rotor transmitters to start to transmit data. The use of electronic distributors is clearly within the scope of the invention. The rotor transmitters transmit during a period while they are in the line of sight of receiver 16. In the showing of FIG. 2, rotor transmitter 27 is finishing its transmission to receiver 16. It will be sequentially followed by the transmission of the rotor transmitters 26, 24, 31, 29 and 28. Each of the transmissions is accomplished while the transmitter is in a line of sight relationship with the receiver 16. As the transmitters arrive at a position during their rotation on the rotor where there is a line of sight relationship between the rotor transmitter and the stator receiver, they are energized to transmit data.

In the embodiment of FIG. 1, the stator 12 is shown as having two receivers 14 and 16. This enables each receiver to define a data channel. Thus, receiver 16 receives data on channel A and receiver 14 receives data on channel B. In the distributor embodiment of FIG. 2, transmitters 27, 26 and 26 first transmit data to receiver 16 on channel A while transmitters 31, 29 and 28 transmit data to receiver 14 on channel B. After transmitter 27 passes from the line of sight of receiver 16 and transmitter 31 leaves the line of sight of receiver 16, data "swapping" occurs. The data swapping results in transmitter 27 starting to transmit data for channel B and transmitter 31 starting to transmit data for channel A.

In an electronic version, the distributor 33 is provided with rotor angle data which it decodes and uses to decide which transmitter must be fed channel A or channel B data. Note that the number of channels can be increased by increasing the number of receivers.

FIG. 1 shows two channels of communication. The distributor of FIG. 2 controls the operation of the rotor transmitter to transmit data to both stator receivers 14 and 16. Alternatively, a separate distributor could be operated with the stator receiver 14. Note that the rotor receiver 23, also shown in FIG. 2, receives signals from the stator transmitters. Among the signals received, may be signals which control the operation of the distributor 33.

Communication between the stator transmitters and the rotor receiver is also done on a line of sight basis. In the configuration of FIG. 1, there is only one channel for transmission of control data going from the stator 12 to the rotor 13. However, in practice more than one channel can be used within the scope of this invention.

FIG. 3 is a simplified showing of the basic arrangement of the communications between the rotor and the stator. Thus, as shown in FIG. 3, rotor transmitter 27 is just at the location where it is in its final stages of its line of sight contact with the stator receiver 16. At this point, the rotor transmitter 26 is also just coming into line of sight contact with the stator receiver 16. A slight overlap in the line of sight contacts between the two transmitters and the receiver assures continuous communication between the rotor and the stator. As the rotor rotates, the other rotor transmitters 24, 31, 29 and 28 will become positioned in a line of sight contact with the stator receiver and will also then transmit to the receiver. A distributor such as distributor 33 will assure that the data is transmitted from a data transmitter that is positioned in line of sight contact with the stator receiver.

FIG. 4C is a schematic block diagram showing of a stator-rotor optical data communication link usable either with a nuclear medicine computerized tomographic system of an X-ray computerized tomographic system. The nuclear medicine tomographic system is schematically shown in FIG. 4A at 41. The X-ray computerized tomographic system is schematically FIG. 4B shown at 42. The nuclear medicine tomographic system includes a gantry 43 which is comprised of an outer stationary portion 44 and an inner rotating portion 46. The rotating portion 46 rotates the gamma camera head or detector unit 47 around a bed 48 holding a patient 49 thereon.

In the gamma camera embodiment of FIG. 6, a light source such as an LED 51 is shown. The light from the LED is modulated by the data obtained from the camera head 47 on the rotating ring 46 portion of the gantry 43. The modulated light beam is then transmitted by a rotor transmitter such as transmitter 26 to a receiver 16 on the stator. The received data on the receiver 16 on the stator is demodulated by demodulator 53. The demodulated data is operated on and processed by the computer 54 to form an image in the display unit 56.

In the X-ray CT gantry, embodiment 42 shows an X-ray source 61 and an arc of detectors 62 mounted on the rotor of the gantry for rotation about the patient 63. The X-rays pass through the patient 63 as the gantry causes at least the X-ray tube to rotate about the patient 63. In the gantry 42, the detector array also rotates and the output of the detector array is transmitted through a rotor transmitter such as rotor transmitter 26 to the stator receiver such as stator receiver 16. The output of stator receiver 16 is then demodulated in unit 53 and the demodulated data is processed in unit 54 for display in unit 56 as previously described.

Means are provided for optimizing the light flux transfer so that signal-to-noise ratio of the photo detector is maximized and at the same time the dynamic range of the light flux variation is minimized. For example, preferably both the transmitters and receivers use cylindrical lenses. The axes of the cylindrical lenses are preferably in the radial direction of the gantry. Note also that the transmitted light is transmitted in a direction transverse to the radial direction and also transverse to a line parallel to the axis of rotation as shown in FIGS. 1 and 3.

To minimize the flux variation, it has been found to be advantageous to mask or otherwise shape a small portion of the receiver lens. This prevents saturating the receiving system. The mask is indicated at strip 38 in FIG. 1 which is a narrow strip of opaque material attached to the face of the cylindrical lens at an area that preferably does not receive maximum light intensity. A means for increasing the light flux reaching the receiver is the use of reflective material on the stator and/or rotor as indicated by the darkened lines 36 and 37 in FIG. 1.

Thus, there is provided a unique communicative link between the rotating portion of the computerized tomographic system and the stator portion of the computerized tomographic system. In operation, line of sight communications between the light transmitters such as LEDs and the light receivers such as photo diodes provide a simple and elegant optical slip ring arrangement for enabling continuous rotation of the rotor of the gantry about the stator of the gantry without the inhibition of cables.

Although modifications and changes may be suggested by those skilled in the art, it is the intention of the inventors to embody within the patent warranted herein all changes and modifications as reasonably properly come within the scope of their contribution to the art.

What is claimed is:

1. A system for transferring data between a rotating part and a stationary part, comprising:
   a rotor,
   a stator spaced apart from said rotor,
   at least one light transmitter mounted on said rotor for transmitting a light beam that is intensity modulated responsive to said data to be transferred between said rotor and said stator,
   at least one light receiver mounted on said stator for receiving and demodulating said intensity modulated light beam transmitted by said at least one light transmitter mounted on said rotor and positioned to enable said transmitted light beam to impinge directly upon said light receiver on a "line of sight" basis for transferring said data from said rotor to said stator,
   a computer processor to process said data to provide image data, and
   an image monitor to provide images based on said image data.

2. The system of claim 1 for transferring data between said rotor and said stator wherein said rotor and stator are parts of a gantry in a medical diagnostic imaging system.

3. The system of claim 2 wherein said medical diagnostic imaging system is an X-ray computerized tomographic imaging system.

4. The system of claim 2 wherein said medical diagnostic imaging system is a single photon emission computerized tomographic system.

5. The system of claim 1 for transmitting data between said rotor and said stator wherein a lens arrangement through which said light is transferred is provided for optimizing light flux transfer of the modulated light beam so as to maximize signal-to-noise ratio in the transfer of the data and minimize the dynamic range of variation of the light flux.

6. The system of claim 5 wherein the lens arrangement for optimizing light flux transfer includes a cylindrical lens in said at least one receiver.

7. The system of claim 5 wherein said lens arrangement comprises a cylindrical lens in said at least one transmitter means.

8. The system of claim 6 wherein the axis of the cylindrical lens is in the radial direction of the gantry.

9. The system of claim 7 wherein said cylindrical lens has an axis that is in the radial direction of said gantry.

10. The system of claim 1 wherein said at least one receiver has a cylindrical lens with a shaped face to reduce optical flux intensity.

11. The system of claim 10 wherein said shaped face comprises an opaque strip attached to the face of said cylindrical lens.

12. The system of claim 1 wherein reflective elements are mounted on said rotor to increase light flux transfer.

13. The system of claim 1 wherein reflective elements are mounted on the stator to increase light flux transfer.

14. The system of claim 6 wherein the light source of said at least one light transmitter comprises LEDs, wherein said LEDs are mounted to transmit light in a direction that is transverse to the radial direction of the gantry and also is transverse to a line parallel to the axis of rotation of the rotor of the gantry, and wherein the axes of the LEDs are at an angle to the optical axis of said lens to optimize the light flux transferred by directing the light beams from the LEDs towards the at least one receiver.

15. The system of claim 2 wherein the light source of said at least one transmitter comprises laser diodes and wherein said laser diodes are mounted to transmit light in a direction that is transverse to the radial direction of the gantry and also is transverse to a line parallel to the axis of rotation of the rotor of the gantry.

16. The system of claim 2 wherein the light source provides light in the infra-red band and wherein said light source is mounted to transmit light in a direction that is transverse to the radial direction of the gantry and also is transverse to a line parallel to the axis of rotation of the rotor of the gantry.

17. The system of claim 1 wherein a first channel comprising at least one transmitter and at least one receiver is provided and wherein at least a second set of at least one transmitter means and at least one receiver means is also provided to increase the number of channels and thereby increase the capacity of data transferable.

18. The system of claim 1 wherein:

a first of said at least one receiver mounted on said stator and a second of said at least one receiver mounted on said rotor, at least one transmitter being mounted on said rotor to form a first channel with said first of said at least one receiver, and a second of said at least one transmitter being mounted on said stator to form a second channel with said second of at least one receiver.

19. The system of claim 18 including means for transferring rotor to stator data in a first circular direction such as clockwise and stator to rotor data in an opposite circulate direction such as counter clockwise to eliminate cross-talk between the channels connecting and rotor to said stator and said stator to said rotor.

* * * * *